United States Patent
Rigby et al.

(10) Patent No.: US 6,489,775 B1
(45) Date of Patent: Dec. 3, 2002

(54) PARTICLE DETECTORS

(75) Inventors: Michael Rigby, Huntingdon (GB); Gary Paul Cullen, Godmanchester (GB)

(73) Assignee: PCME Ltd., Cambridgeshire (GB)

(*) Notice: Subject to any disclaimer, the term of this patent is extended or adjusted under 35 U.S.C. 154(b) by 0 days.

(21) Appl. No.: 09/647,185

(22) PCT Filed: Mar. 26, 1999

(86) PCT No.: PCT/GB99/00955
§ 371 (c)(1),
(2), (4) Date: Dec. 20, 2000

(87) PCT Pub. No.: WO99/50641
PCT Pub. Date: Oct. 7, 1999

(30) Foreign Application Priority Data

Mar. 27, 1998 (GB) .............................................. 9806633

(51) Int. Cl.$^7$ ............................................. G01N 27/60
(52) U.S. Cl. ..................... 324/454; 324/71.1; 73/861.08
(58) Field of Search ................................. 324/454, 71.1, 324/21.5, 72; 73/861.08; 340/607, 627

(56) References Cited

U.S. PATENT DOCUMENTS

| | | | |
|---|---|---|---|
| 4,179,934 A | 12/1979 | Svarovsky | 73/865.5 |
| 4,594,553 A * | 6/1986 | Varga | 324/454 |
| 4,607,228 A * | 8/1986 | Reif | 324/545 |
| 4,888,948 A | 12/1989 | Fisher et al. | 324/454 |
| 5,095,275 A * | 3/1992 | Dechene | 324/454 |
| 5,287,061 A | 2/1994 | Dechene et al. | 324/454 |
| 5,591,895 A * | 1/1997 | Rigby | 324/454 |

FOREIGN PATENT DOCUMENTS

| | | |
|---|---|---|
| DE | 1 122 292 | 1/1962 |
| EP | 0 110 802 A2 | 10/1983 |
| WO | WO 94/25865 | 11/1994 |

* cited by examiner

*Primary Examiner*—Christine K Oda
(74) *Attorney, Agent, or Firm*—Pitney, Hardin, Kipp & Szuch LLP

(57) ABSTRACT

A particle detector for detecting particles flowing in a duct has a first triboelectric probe (5) for detecting the particles and a second triboelectric probe (3) for detecting a signal generated by contaminants on the particle detector. The presence of signal-generating contaminants on the particle detector will result in an error signal on the first probe (5) and a signal on the second probe (3). Therefore, the presence of a signal on the second probe (3) will indicate that the signal appearing on the first probe (5) includes an error signal. If the ratio of the magnitude of the signal generated on the second probe (3) to the magnitude of the signal generated on the first probe (5) exceeds a certain pre-defined limit, cleaning of the detector will be required.

24 Claims, 3 Drawing Sheets

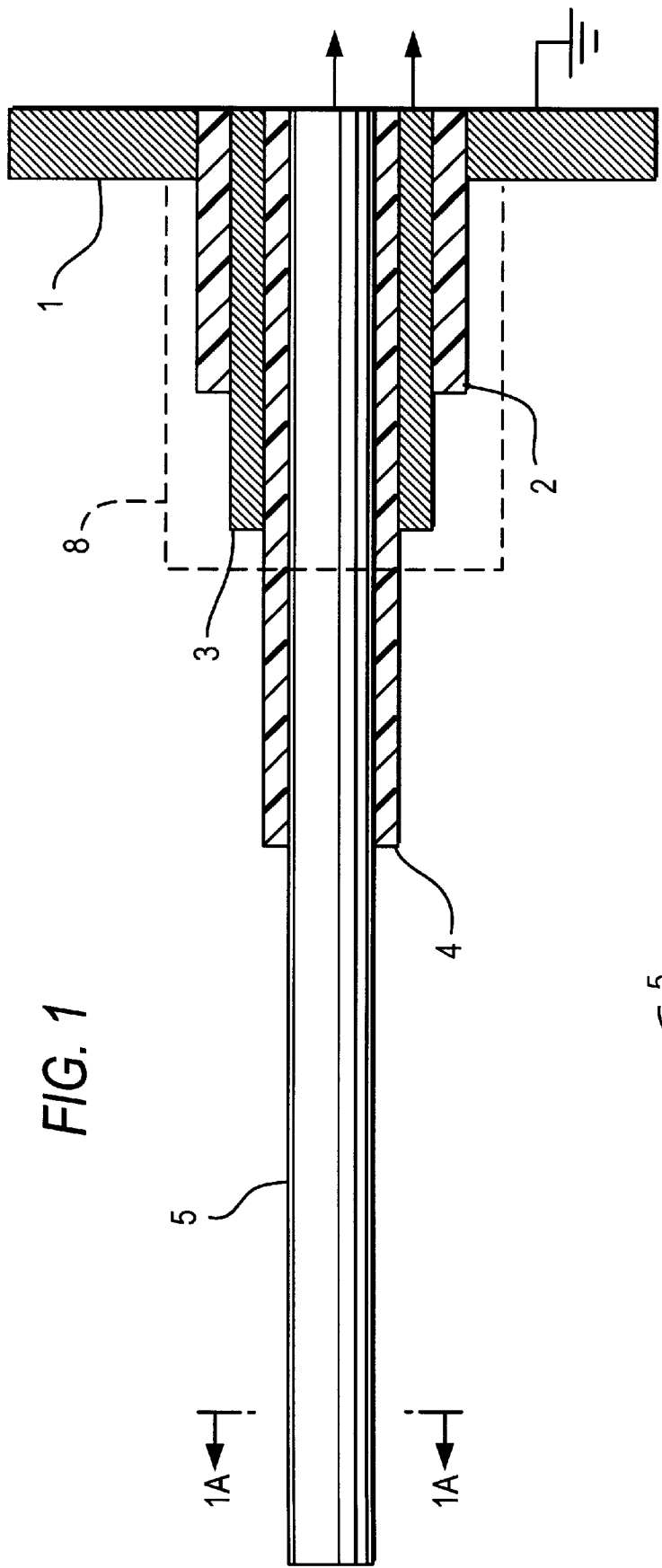
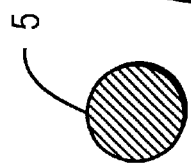

PARTICLE DETECTORS

BACKGROUND OF THE INVENTION

1. Field of the Invention

The invention relates to apparatus for detecting particles flowing in a duct and a method of detecting contaminants on the particle detector.

2. Description of the Prior Art

The performance of a triboelectric particle detector may be impaired if particles from the flow are allowed to build up on its surface. One way to avoid the build up of particles is to clean the probe on a regular basis. However, cleaning involves taking the particle detector off-line and may be time-consuming and require the disassembly of complex equipment. It is therefore desirable to monitor the level of contamination of the detector.

U.S. Pat. No. 5,287,061 describes an on-line method of monitoring a detector for contamination. In the method described in that patent, a detector in the form of a probe is triboelectrically charged by particles in a flow. The signal generated by that charging passes through monitor circuitry that includes an amplifier, the gain of which is dependent upon the impedance of the probe. Under normal operating conditions, the impedance of the probe is substantially infinite. However, when the probe becomes contaminated the impedance may drop significantly, and that drop results in a change in the gain of the amplifier. In order to detect the occurrence of any such change in gain, a second signal of known amplitude is passed through the amplifier. A change in the magnitude of the amplified second signal indicates that the gain of the amplifier has changed and that cleaning of the probe may be required.

A low probe impedance can also cause the gain of the amplifier to rise with respect to the amplifier's internal noise; i.e., the gain seen by the input signal is unchanged, but the gain seen by the internal noise is increased. That causes an increase in the background noise level of the instrument, and that increase may be enough to mask low-level signals.

However, a finite probe impedance does not always cause a problem in a particle detection system. In particular, in a detector in which A.C. coupling is used, such as those described in British Patent No. 2266772 and British Patent No. 2277154, a finite probe impedance usually only has a significant effect if it is so low as to saturate the amplifier, or if it varies in magnitude with time. Each of those effects would produce an error signal with an A.C. component which would be detected by the A.C. monitoring apparatus. In most other circumstances a finite impedance would usually only result in a D.C. signal caused by the offset-error voltage of the amplifier. The A.C. coupling circuitry would filter out such a D.C. signal.

A more significant problem for both A.C.- and D.C.-coupled detectors occurs when contaminants on the detector act as a signal source. Particles flowing past the detector can interact with the contaminants and cause the generation of A.C. or D.C. error signals. The impedance-dependent contamination monitoring technique described above would not detect signal-generating contamination unless the contamination also resulted in a low probe impedance.

It is an object of the invention to provide a method and apparatus for detecting particles flowing in a duct and for detecting contamination which is acting as a signal on the particle detector.

SUMMARY OF THE INVENTION

According to the invention, there is provided a particle detector for detecting particles flowing in a duct, comprising: a first triboelectric probe for detecting the particles and a second triboelectric probe for detecting a signal generated by contaminants on the particle detector.

The first probe may be used for monitoring the particle flow in the usual way. The presence of signal-generating contaminants on the particle detector will result in an error signal on the first probe. The error signal will also be detected on the second probe because the second probe is located between the first probe and the structure. Therefore, the presence of a signal on the second probe will indicate that the signal appearing on the first probe includes an error signal. The degree to which contamination is a problem may be determined by considering the ratio of the magnitude of the signal generated on the second probe to the magnitude of the signal generated on the first probe. If this ratio exceeds a certain pre-defined limit then cleaning of the detector will be required.

Advantageously, the second probe substantially surrounds the first probe. Each of the first and second probes may take any of several forms; for example, at least one of the probes may be in the form of a rod (which may be of circular cross-section), a ring or a stud.

The particle detector may be so arranged that, if the detector is mounted on a duct, both probes will project into a flow of particles flowing in the duct. Alternatively, the particle detector may be so arranged that, if the detector is mounted on a duct, neither probe will project into a flow of particles flowing in the duct. Preferably, the particle detector is so arranged that, if the detector is mounted on a duct, the second probe does not project into a flow of particles flowing in the duct. If both probes project into the particle flow, the second probe should be so arranged that it generates a significantly smaller signal attributable to the particle flow than the signal generated by the first probe. The ratio of the signals from the two probes would remain approximately constant when the detector was not contaminated, but a ratio significantly different from that constant value would indicate that the detector was contaminated. Even with the second probe out of the air stream, it is possible that the second probe will detect a low-level signal attributable to the flow of particles.

Also according to the invention there is provided apparatus for detecting particles flowing in a duct, the apparatus comprising: a particle detector, which includes a first probe and a second probe, the first and second probes being so arranged that, if the particle detector is mounted on a structure, the second probe will be positioned between the first probe and the structure, and the first and second probes will be substantially electrically isolated from each other and from the structure; means for monitoring a signal generated on the first probe; and means for monitoring a signal generated on the second probe by contaminants on the detector.

The means for monitoring the signal generated on the second probe may be electronic circuitry substantially identical in design to that used to monitor the signal generated on the first probe. The means for monitoring the signal generated on the second probe may be substantially independent of the means for monitoring the signal generated on the first probe. Alternatively, the means for monitoring the signal generated on the second probe may utilise the means for monitoring the signal generated on the first probe.

The monitoring means may include means to monitor A.C. components of the signals and may furthermore include filtering circuitry which removes D.C. components from the signals. Alternatively, the monitoring means may include means to monitor D.C. components of the signals.

Also according to the invention, there is provided a particle-detecting installation, including a duct together with a particle detector as described above. Also according to the invention, there is provided a particle-detecting installation, including an apparatus for detecting particles as described above. Both probes may project into the flow of particles. Alternatively, neither probe projects into the flow of particles, Preferably, the second probe does not project into the flow of particles. The duct may be a stack.

Also according to the invention, there is provided a method of detecting contaminants on a particle detector, which involves the use of a particle detector as described above. Also according to the invention, there is provided a method of detecting contaminants on a particle detector, which involves the use of an apparatus for detecting particles as described above. Also according to the invention, there is provided a method of detecting contaminants on a particle detector, which involves the use of a particle detecting installation, as described above.

The present invention also provides a method of detecting contaminants on a particle detector comprising: providing a particle detector, which comprises a first triboelectric probe for detecting particles flowing in a duct and a second triboelectric probe; monitoring a signal generated on the first probe; and monitoring a signal generated on the second probe by the contaminants.

The signal from the second probe may be monitored continuously via monitoring circuitry that is substantially independent of monitoring circuitry used to monitor the signal from the first probe. Alternatively, the signal from the second probe may be monitored intermittently via monitoring circuitry used to monitor the signal from the first probe, with the monitoring circuitry being switched between the two probes. The latter method requires less circuitry but the former enables monitoring to be carried out more frequently without taking the first probe off-line.

Preferably, A.C. components of the signals generated on the first and second probes are monitored. Alternatively, the D.C. components of the signals generated on the first and second probes may be monitored. Alternatively, the signals including both A.C. and D.C. components may be monitored.

The present invention also provides a method of detecting contaminants on a particle detector, the method comprising: providing a particle detector, which is mounted on a structure and includes a first triboelectric probe and a second triboelectric probe, which is positioned between the first probe and the structure, the first and second probes being substantially electrically isolated from each other and from the structure; and monitoring a signal generated on the second probe by the contaminants.

BRIEF DESCRIPTION OF THE DRAWINGS

Apparatus for detecting contaminants on a particle detector in accordance with the invention will now be described, by way of example only, with reference to the accompanying drawings in which:

FIG. 1 is a cross-sectional view of a particle detector according to the invention FIG. 1A is a cross-sectional view taken as indicated in FIG. 1.

DETAILED DESCRIPTION OF THE PREFERRED EMBODIMENTS

Figure 2:
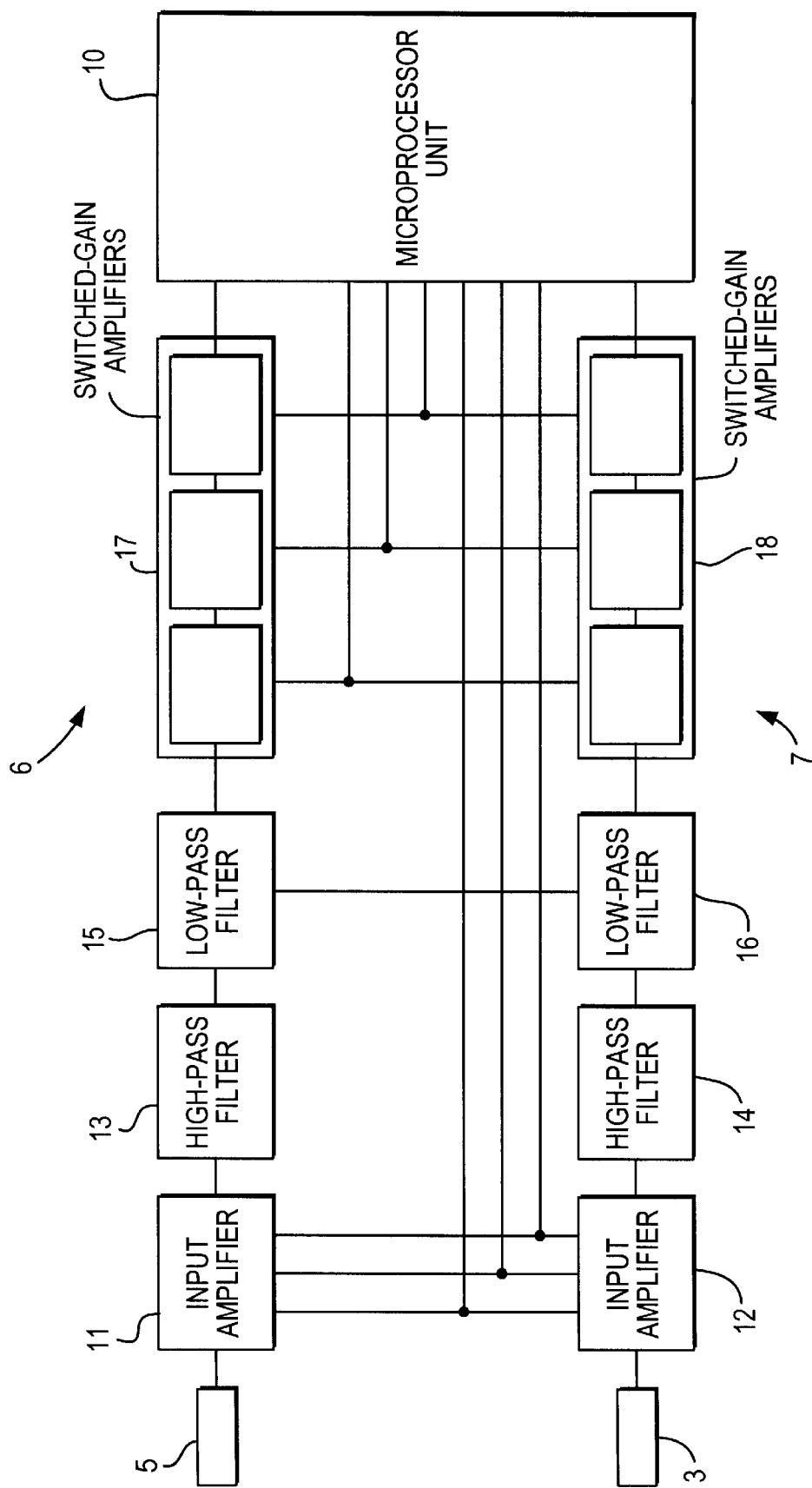
FIG. 2 is a schematic representation of the signal processing circuitry used to perform the detector-contamination check.

The particle detector shown in FIG. 1 consists of a first probe 5 and a second probe 3 which are mounted in the wall of a stack 1 so as to project into a flow of particles within the stack. The first 5 and second 3 probes are electrically isolated from each other by a first insulating layer 4, and the second probe 3 is electrically isolated from the stack wall 1 by a second insulating layer 2. The wall of the stack is regarded as zero electrical potential; that is, it is the electrical reference potential.

In FIG. 1, optional shield 8 is included where it is desired to keep second probe 3 from projecting into the flow of particles in the duct.

FIG. 1A is a cross-sectional view taken as indicated in FIG. 1 and showing the first probe 5 to have a circular cross section.

If the particle detector is contaminated by contaminants which act as a signal source, the contaminants serve as a voltage or current source, with one connection to the first probe 5 and the other to the stack wall 1 (and hence ground). That voltage or current source will also generate a signal on the second probe 3, since the second probe 3 is located between the first probe 5 and the stack wall 1. The second probe 3 will therefore generate a signal if an error signal which is attributable to contamination of the detector is generated on the first probe 5.

The signals from the detector are monitored by the apparatus shown in FIG. 2. Signals from the first probe 5 are filtered and amplified in the main amplifier channel 6 and signals from the second probe 3 are filtered and amplified by the check-probe amplifier channel 7. A microprocessor unit 10 so controls the channels as to maintain the same level of gain and sensitivity in each.

In this described embodiment of the invention, the same electronics is used in each of the amplifier channels. The signals from the probes 3,5 pass first to input amplifiers 11,12 which provide output voltages from the input signals. The sensitivity of the input amplifiers 11,12 may be adjusted, and that adjustment is controlled by the microprocessor unit 10. Sensitivity adjustment allows the apparatus to be used in processes covering a very wide range of particle-flow levels, with the sensitivity being adjusted according to the particle-flow level of the process. The sensitivity is typically fixed during instrument installation.

The signals next pass through high-pass filters 13,14, which filter out the D.C. component of the signals, together with A.C. components at frequencies of up to some upper frequency limit. In a particular example of the invention, that limit might be about 0.1 Hz, but the value of the limit should be chosen to be appropriate for the process in which the apparatus is used.

The signals then pass through low-pass filters 15,16 which remove high-frequency components of the signals, including high-frequency interference signals. Low-pass filtering helps to make the apparatus more robust in industrial environments.

The signals then pass to switched-gain amplifiers 17, 18, which are used to improve the ability of the apparatus to accommodate the widely varying particle-flow levels seen in some processes; for example, in bag filter applications using reverse air jet cleaning, where very high amplitude pulses of particles may be seen during the cleaning cycle. Each component amplifier (three are shown in each of the two amplifier blocks in FIG. 2) is an A.C. amplifier with a gain that may independently be switched from 1 to 16. The amplifier gains are adjusted dynamically by the microprocessor unit 10 during normal system operation: the microprocessor unit 10 changes the gain of the amplifiers 17,18 in response to variations in the dust level.

The signals from the amplifiers 17,18 pass to the microprocessor unit 10. In that unit, the signals are compared and, if the signal from the check-probe amplifiers 18 is significant when compared with the signal from the main amplifiers 17, the user is alerted that the probe is contaminated. The error:signal ratio threshold at which the operator is alerted may need to be adjusted according to the signal level, since, at low levels, background noise may become significant enough to cause the two signal levels to be approximately equal, whereas, at higher levels, substantially the whole of each signal will be attributable to particle flow or detector contamination.

Although the specific embodiment which has been described above utilises circuitry which monitors the A.C. components of the signals from the probes, the invention could also be embodied in a system in which the D.C. component of each of the signals is monitored.

Figure 2A:
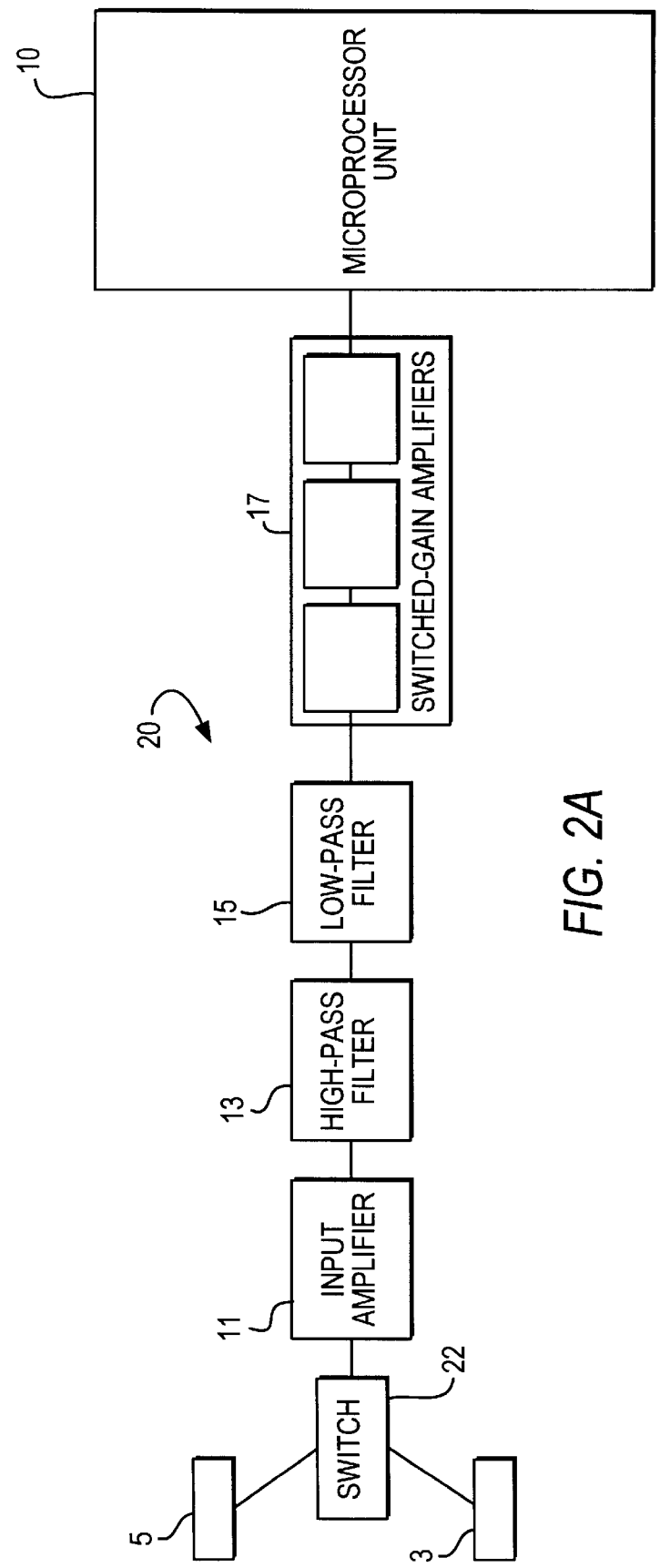
FIG. 2A is a schematic representation of an alternate signal processing circuitry.

Moreover, FIG. 2A shows an alternate apparatus 20 in which the first probe 5 and the second probe 3 are monitored by the same electronic circuitry, the circuitry being switched intermittently between the two probes 3,5 by switch 22.

What is claimed is:

1. A particle detector for detecting particles flowing in a duct, comprising: a first triboelectric probe for detecting the particles and a second probe, the first and second probes being arranged relative to one another such that, if the particle detector is contaminated by contaminants that generate a signal on the first probe, the contaminants also generate a signal on the second probe, wherein the second probe substantially surrounds the first probe over at least a portion of the length of the first probe.

2. A particle detector as claimed in claim 1, in which at least one of the probes is in the form of a rod.

3. A particle detector as claimed in claim 2, in which the rod is of circular cross-section.

4. A particle detector as claimed in claim 1, in which at least one of the probes is in the form of a ring.

5. A particle detector as claimed in claim 1, the particle detector including mounting means so arranged that, if the detector is mounted on said duct, said first and second probes will project into a flow of particles flowing in said duct.

6. A particle detector as claimed in claim 1, the particle detector including mounting means so arranged that, if the detector is mounted on said duct, the second probe will not project into a flow of particles flowing in said duct.

7. A particle-detecting installation, including a duct and a particle detector according to claim 1.

8. The particle-detecting installation as claimed in claim 7, in which said first and second probes project into the flow of particles.

9. A particle-detecting installation as claimed in claim 7, in which the second probe does not project into the flow of particles.

10. A particle-detecting installation as claim 7, in which the duct is a stack.

11. A method of detecting contaminants on a particle detector, which involves the use of a particle-detecting installation according to claim 7.

12. A method of detecting contaminants on a particle detector, which involves the use of a particle detector according to any of claim 1.

13. Apparatus for detecting particles flowing in a duct, the apparatus comprising: a particle detector, which includes a first probe and a second probe, the first and second probes being arranged relative to one another such that, if the particle detector is mounted upon a structure, the second probe will be positioned between the first probe and the structure, the first and second probes will be substantially electrically isolated from each other and from the structure and, if the particle detector is contaminated by contaminants that generate a signal on the first probe, the contaminants will also generate a signal on the second probe; means for monitoring said signal generated on the first probe; and means for monitoring said signal generated on the second probe by the contaminants on the detector.

14. Apparatus as claimed in claim 13, in which the means for monitoring the signal generated on the second probe is electronic circuitry substantially identical in design to that used to monitor the signal generated on the first probe.

15. Apparatus as claimed in claim 13, in which the means for monitoring the signal generated on the second probe is substantially independent of the means for monitoring the signal generated on the first probe.

16. Apparatus as claimed in claim 13, in which the means for monitoring the signal generated on the second probe utilises the means for monitoring the signal generated on the first probe.

17. Apparatus as claimed in claim 13, in which the means for monitoring the signals generated by the first and second probes include means to monitor A.C. components of said signals.

18. A particle-detecting installation, including an apparatus for detecting particles flowing in a duct according to any of claim 13.

19. A method of detecting contaminants on a particle detector, which involves the use of an apparatus according to any of claim 8.

20. A method of detecting contaminants on a particle detector comprising: providing a particle detector, which comprises a first triboelectric probe for detecting the particles flowing in a duct and a second probe, in which the second probe substantially surrounds the first probe over at least a portion of the length of the first probe, the first and second probes being arranged relative to one another such that, if the particle detector is contaminated by contaminants that generate a signal on the first probe, the contaminants also generate a signal on the second probe; monitoring said signal generated on the first probe; and monitoring said signal on the second probe by the contaminants.

21. A method as claimed claim 20, in which the signal from the second probe is monitored continuously via monitoring circuitry that is substantially independent of monitoring circuitry used to monitor the signal from the first probe.

22. A method as claimed claim 20, in which the signal from the second probe is monitored intermittently via monitoring circuitry used to monitor the signal from the first probe.

23. A method as claimed in any of claims 20, in which A.C. components of-the-signals generated on the first and second probes are monitored.

24. A method of detecting contaminants on a particle detector, the method comprising: providing the particle detector, which is mounted on a structure and includes a first triboelectric probe and a second probe, which is positioned between the first probe and the structure, the first and second probes being substantially electrically isolated from each other and from the structure and being arranged relative to one another such that, if the particle detector is contaminated by contaminants that generate a signal on the first probe, the contaminants will also generate a signal on the second probe; monitoring said signal generated on the second probe by the contaminants.

* * * * *